United States Patent [19]
Bartke et al.

[11] Patent Number: 5,545,533
[45] Date of Patent: Aug. 13, 1996

[54] MONOCLONAL ANTIBODIES AGAINST C-KIT AND METHOD OF DETECTING A MALIGNANCY USING C-KIT SPECIFIC ANTIBODIES

[75] Inventors: Ilse Bartke, Tutzing; Gunter Kostka, Munich; Kurt Naujoks, Penzberg; Axel Ullrich, Munich, all of Germany

[73] Assignee: Boehringer Mannheim GmbH, Mannheim, Germany

[21] Appl. No.: 469,778

[22] Filed: Jun. 6, 1995

Related U.S. Application Data

[63] Continuation of Ser. No. 142,330, Nov. 26, 1993, abandoned.

[30] Foreign Application Priority Data

May 25, 1991 [DE] Germany .................. 41 17 090.3
Feb. 20, 1992 [DE] Germany .................. 42 05 148.7

[51] Int. Cl.⁶ ................ G01N 33/53; C07K 16/32; C12N 5/20
[52] U.S. Cl. ............. 435/723; 435/240.27; 435/70.21; 530/387.7; 530/388.85; 530/388.7; 530/388.73
[58] Field of Search ............. 530/387.7, 388.22, 530/388.73, 388.75, 388.8, 388.85, 170.21, 172.2; 435/240.27, 724, 725

[56] References Cited

FOREIGN PATENT DOCUMENTS

89/01973  3/1989  WIPO.

OTHER PUBLICATIONS

Waldmann, Science 252:1657–1662, 1991.
Harris et al., Tibtech 11:42–44, 1993.
Lerner et al., Blood 77:1876–1883, 01 May 1991.
Broudy et al. Blood 79(2):338–346, 1992 (15 Jan.)
Gadd et al. Leukemia Research 9:1329–1336, 1985.
Buhring et al. Cancer Res 53:4424–31 15 Sep. 1993.
Buhring et al. Leukemia 5:854–859, 1991 (Oct.).
Harlow et al. "Antibodies A Laboratory Manual" Cold Spring Harbor Laboratory, 1988 p. 287.
Mendelsohn, in "Monoclonal Antibody Therapy", H. Waldmann Ed., Kanger 1988 pp. 147–160.
Sato et al. Mol. Biol. Med. 1:511–579, 1983.
Gordon et al. in "Handbook of Experimental Immunology" vol. 2.
Weir et al. Eds., Blackwell Scientific Publ., 1986, pp. 43.1–43.15.
Ashman et al. J. Cellular Physiology 158:545–554, 1994.
Hirata et al. J. Immunology 143:2900–2906, 1989.
Strohmeyer et al. Cancer Res. 51:1811–1816, 1991.
Yarden et al., Embo Journal, "Human proto-oncogene c-kit: a new cell surface receptor tyrosine kinase for an unidentified ligand", vol. 6, No. 11, pp. 3341–3351, 1987.
Ashman, Journal of Cellular Biochemistry, "A murine monoclonal antibody to the human c-kit proto-oncongene product SCF receptor effect on the growth of hemopoietic ürogenitor cells in-vitro and expression of c-kit in AML.," Supplement 15F, 1991.
L. Ashman et al., Leukemia Research, vol. 14, No. 7, pp. 637–644, 1990.
V. C. Broudy et al., Clinical Research, vol. 39, No. 2, 1991.

*Primary Examiner*—Paula K. Hutzell
*Attorney, Agent, or Firm*—Nikaido, Marmelstein, Murray & Oram LLP

[57] ABSTRACT

The invention concerns monoclonal antibodies against the human c-kit receptor which are obtainable from the cell lines DSM ACC 2007, DSM ACC 2008 and DSM ACC 2009 or are capable of binding to the c-kit receptor in an equivalent manner to the antibodies produced by the cell lines DSM ACC 2007, DSM ACC 2008 or DSM ACC 2009. The present invention also concerns a method for testing the malignancy of tumours of haematopoietic cells, of seminomas or small-celled lung carcinoma in which a tissue sample is incubated with at least one monoclonal antibody against the c-kit receptor according to the present invention and subsequently bound antibodies are detected by means of known methods.

4 Claims, 1 Drawing Sheet

MONOCLONAL ANTIBODIES AGAINST C-KIT AND METHOD OF DETECTING A MALIGNANCY USING C-KIT SPECIFIC ANTIBODIES

This application is a continuation division of application Ser. No. 08/142,330 filed Nov. 26, 1993 (abandoned). Which is the National Phase of PCT/EP92/01117 filed May 25, 1992.

The invention concerns monoclonal antibodies against the human c-kit receptor as well as a method for testing the malignancy of tumours of haematopoietic cells, of seminomas or small-celled lung carcinoma by detecting a change in the expression of the c-kit receptor.

The development, differentiation and metabolic functions of cells of a multicellular organism are regulated by hormones and growth factors. The first step in many cases is binding of these factors to a receptor on the cell surface. For several of these receptors this binding triggers the phosphorylation of tyrosine residues of various cell proteins. It was possible to show that these receptor-tyrosine kinases have a decisive influence on the growth behaviour of cells (Yarden and Ullrich, Ann. Rev. Biochem. 57 (1988), 443–478). Autocrine regulation systems involving receptor-tyrosine kinases play an important role in the transformation of cell lines which serve as model systems for tumours and also in primary tumour tissue. In the case of certain receptor-tyrosine kinases such as the EGF receptor and the her2/ neu receptor, a direct relation between overexpression of the receptor and the aggressiveness of the tumour process has been proven (Slamon et al., Science 244, 1989, 707–712; Di Fiore et al., Cell 51, 1987, 1063–1070).

A further member of the receptor-tyrosine kinase family is c-kit which was discovered, cloned and sequenced as a cellular homologue of the viral oncogene v-kit (feline leukemia virus HZ4-FeSV; Yarden et al., EMBO Journal 6 (1987), 3341–3351). It has a substantial homology to the PDGF receptor and to the CSF-1 receptor (c-fms). Investigations using the Northern Blot technique indicate a characteristic distribution of the receptor in different tissues. A high expression of the c-kit gene was detected in haematopoietic cells and above all in brain tissues, melanoblasts, ovaries and in stem cells of the testis (Orr-Urtreger et al., Development 109 (1990), 911–923). Investigations on various erythroid and myeloid cell lines indicate an expression of the c-kit gene in early stages of differentiation (André et al., Oncogene 4 (1989), 1047–1049). Certain tumours such as e.g. glioblastoma cells likewise exhibit a pronounced expression of the c-kit gene.

In the meantime a protein of about 30 kD in size was isolated from the culture supernatant of murine fibroblasts as the natural ligand of the c-kit receptor and has been designated MGF= mast cell growth factor (Williams et al., Cell 63 (1990), 167–174) or haematopoietic growth factor KL (Huang et al., Cell 63, (1990), 225–233). A corresponding protein was also isolated from rat liver cells and designated SCF= stem cell factor (Zsebo et al., Cell 63 (1990), 195–201). The corresponding human factor was cloned by Martin et al. and is designated synonymously SCF, MGF or Steel Factor (SF) (Cell 63 (1990), 203–211).

Up to now the expression of the c-kit gene was only determined on the transcription level by the detection of c-kit mRNA, in particular with the aid of the Northern Blot technique. This method can, however, only give indirect indications about the amount of expressed protein since e.g. regulation processes on a translational level or the stability of the c-kit receptor protein which is formed are not registered at all. Therefore for diagnostics it is of decisive importance to directly determine the amount of expressed protein. This is only possible with the required specificity of the result using monoclonal antibodies against the c-kit receptor.

N. Lerner et al., (Blood 77 (1991), 1876–1883) showed that the monoclonal antibody YB5.B8 of Gadd et al., (Leuk. Res. 9 (1985), 1329) which is directed against leukaemic blasts of a patient with acute myeloid leukemia probably reacts with the c-kit protein. However, a monoclonal antibody against the c-kit receptor can only be obtained with absolute certainty by immunization with a defined c-kit antigen.

The object of the invention was therefore to provide monoclonal antibodies against the c-kit receptor as well as a process for their production, and to provide a method which, using these antibodies, enables detection of changes in the expression of this c-kit receptor.

This object is achieved by monoclonal antibodies against the human c-kit receptor which are obtainable from the cell lines DSM ACC 2007, DSM ACC 2008 or DSM ACC 2009 or which are capable of binding in an equivalent manner to the c-kit receptor as the antibodies produced by the cell lines DSM ACC 2007, DSM ACC 2008 or DSM ACC 2009.

Figure 1:
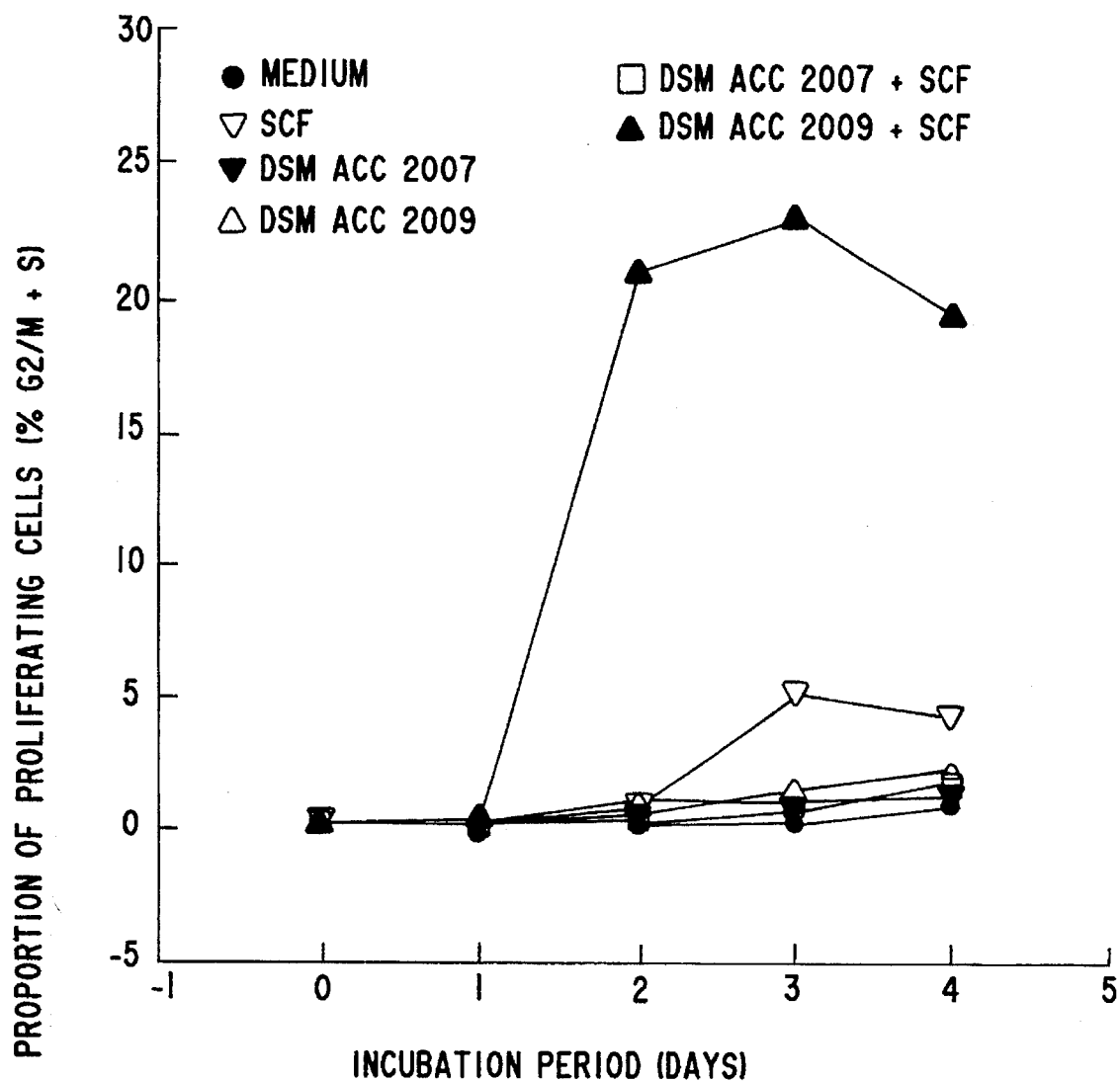
FIG. 1 shows the stimulation of SCF induced proliferation of lymphoid cells by monoclonal antibody DSM ACC 2009, and the inhibition of the SCF induced proliferation of lymphoid cells by the monoclonal antibody DSM ACC 2007.

The term "antibodies capable of binding in an equivalent manner" is understood as antibodies in which there is a detectable epitope overlap with the defined known antibody. This epitope overlap can easily be detected using a competitive test system. For this an enzyme immunoassay is used for example to examine to what extent an antibody competes with the known antibody for binding to a defined antigen or to a special epitope. For this the appropriate antigen is incubated with the known monoclonal antibody in a labelled form and with an excess of the antibody under consideration. It can then be easily established to what extent the antibody under consideration can displace the defined antibody from the binding by immobilizing the complexes formed, separating the solid from the liquid phase and detecting the bound label in one of the two phases. If there is a displacement of at least 50% at a $10^5$-fold excess then an epitope overlap is present.

It has surprisingly turned out that the antibodies obtained react specifically only with seminomas (DSM ACC 2008) or seminomas and small-celled lung carcinoma (DSM ACC 2007 and DSM ACC 2009) but not with healthy lung tissue.

In addition it has also surprisingly turned out that the monoclonal antibody DSM ACC 2007 inhibits stimulation of the proliferation of lymphoid cells by the stem cell factor SCF. This antibody also inhibits binding of growth factors such as SCF to the c-kit receptor and thus also the SCF-induced phosphorylation of the c-kit receptor as well as the SCF-induced decrease in the expression of c-kit receptor molecules.

The invention therefore also concerns a monoclonal antibody against the human c-kit receptor which inhibits binding of growth factors to the c-kit receptor and is obtainable by immunization with mammalian cells which have been transfected with a c-kit sequence that can be expressed in these cells, immortalizing the spleen cells of the immunized animals, identifying those hybridoma cells which produce the desired antibody by determining the binding of the antibody obtained to the c-kit receptor as well as by determining the effect of this antibody on the binding of growth factors to the c-kit receptor, identifying those hybridoma cells whose culture supernatant has an inhibitory effect in this process, cloning these hybridoma cells and isolating the antibodies produced by these clones according to known methods.

The invention preferably concerns a monoclonal antibody against the human c-kit receptor which inhibits the stimulation of the proliferation of lymphoid cells by SCF and is obtainable by immunizing with mammalian cells which have been transfected with a c-kit sequence that can be expressed in these cells, immortalizing the spleen cells of the immunized animals, identifying those hybridoma cells which produce the desired antibody by determining the binding of the antibody obtained to the c-kit receptor as well as by determining the effect of this antibody on the proliferation of lymphoid cells, identifying those hybridoma cells whose culture supernatant shows an inhibitory effect in this process, cloning these hybridoma cells and isolating the antibodies produced by these clones according to known methods.

The immunization is carried out in animals which are usually used for this purpose such as e.g. mice or rats. Mice are preferably used.

NIH-3T3 cells which have been transfected with a cDNA coding for the c-kit protein are preferably used as the immunogen. This cDNA was cloned as described by Yarden et al. (EMBO J. 6 (1987), 3341–3351). The transfected NIH-3T3 cell line c-kit used for the immunization was deposited on the 23.05.1991 at the "Deutsche Sammlung von Mikroorganismen und Zellkulturen GmbH" under the deposit number DSM ACC 2006.

The spleen cells of the immunized animals are preferably immortalized by fusion with the myeloma cell line P3X63–Ag8.653 (ATCC CRL 1580) according to the method in J. of Imm. Meth. 39 (1980) 285–308. Apart from this, other methods familiar to a person skilled in the art can also be used to immortalize spleen cells (e.g. EBV transformation).

For the cloning, the cells are separated for example by means of a fluorescence-activated cell sorter. In order to detect immortalized cells which produce the desired antibody against c-kit, a sample of the culture supernatant is tested in an ELISA test for reactivity with the c-kit receptor. In order to obtain those antibodies which inhibit binding of growth factors to the c-kit receptor or inhibit the stimulation of the proliferation of lymphoid cells by SCF, the culture supernatant of those clones which produce the antibodies binding to the c-kit receptor are in addition examined for inhibition of growth factor binding to the c-kit receptor and inhibition of SCF-stimulated proliferation of lymphoid cells.

The inhibition of growth factor binding to the c-kit receptor is usually carried out by incubating a labelled growth factor with the c-kit receptor in the presence of the antibody to be examined and subsequently determining receptor-bound growth factor.

The inhibition of SCF-induced proliferation of lymphoid cells is determined in the usual manner, preferably by means of fluorescence labelling of lymphocytes whose proliferation has been stimulated with SCF.

Those clones whose culture supernatant shows a positive reaction are expanded and the antibodies produced by these clones are isolated according to known methods.

It has surprisingly turned out that the antibody DSM ACC 2007 binds to the c-kit receptor treated with paraffin as well as to the c-kit receptor which has not been treated with paraffin.

In a preferred embodiment of the invention those hybridoma cells are cloned whose culture supernatant contains those antibodies which also react with the paraffin-treated c-kit receptor and the antibodies produced by these clones are isolated according to known methods.

The detection of immortalized cells which produce the desired antibody against c-kit is carried out in this preferred embodiment by incubating a sample of the culture supernatant with a paraffin-treated tissue section and detecting the antibody bound to the c-kit receptor present in this tissue section.

Surprisingly the monoclonal antibody DSM ACC 2009 synergistically stimulates the proliferation of lymphoid cells induced by the stem cell factor SCF. In addition it stimulates the SCF-induced phosphorylation of the c-kit receptor and causes a slight delay in the SCF-induced decrease of c-kit receptor expression.

The invention therefore in addition concerns a monoclonal antibody against the human c-kit receptor which stimulates the SCF-induced proliferation of lymphoid cells and is obtainable by immunizing with mammalian cells which have been transfected with a c-kit sequence that can be expressed in these cells, immortalizing the spleen cells of the immunized animals, identifying those hybridoma cells which produce the desired antibody by determining the binding of the antibody obtained to the c-kit receptor as well as by determining the effect of this antibody on the proliferation of lymphoid cells, identifying those hybridoma cells whose culture supernatant has a stimulating effect in this process, cloning these hybridoma cells and isolating the antibody produced by these clones according to known methods.

The stimulation of the SCF-induced proliferation of lymphoid cells is determined in the usual manner, preferably by means of fluorescence labelling of lymphocytes whose proliferation has been stimulated with SCF.

The invention in addition concerns a process for the production of monoclonal antibodies against the human c-kit receptor by immunizing with mammalian cells which have been transfected with a c-kit sequence that can be expressed in these cells and immortalizing the spleen cells of the immunized animals whereby those hybridoma cells are cloned which produce antibodies against the human c-kit receptor and the antibodies produced by these clones are isolated according to known methods.

The invention also preferably concerns a process for the production of monoclonal antibodies against the human c-kit receptor which inhibit binding of growth factors to the c-kit receptor and are obtainable by immunizing with mammalian cells which have been transfected with a c-kit sequence that can be expressed in these cells, immortalizing the spleen cells of the immunized animals, identifying those hybridoma cells which produce the desired antibody by determining the binding of the antibody obtained to the c-kit receptor and by determining the effect of this antibody on the binding of growth factors to the c-kit receptor, identifying those hybridoma cells whose culture supernatant has an inhibitory effect in this process, cloning these hybridoma cells and isolating the antibodies produced by these clones according to known methods.

The invention particularly preferably concerns a process for the production of monoclonal antibodies against the human c-kit receptor which inhibit the stimulation of the proliferation of lymphoid cells by SCF and are obtainable by immunizing with mammalian cells which have been transfected with a c-kit sequence that can be expressed in these cells, immortalizing the spleen cells of the immunized animals, identifying those hybridoma cells which produce the desired antibody by determining the binding of the antibody obtained to the c-kit receptor as well as by determining the effect of this antibody on the proliferation of lymphoid cells, identifying those hybridoma cells whose culture supernatant has an inhibitory effect in this process, cloning these hybridoma cells and isolating the antibodies produced by these clones according to known methods.

The invention in addition particularly preferably concerns a process for the production of monoclonal antibodies against the human c-kit receptor which stimulate the SCF-induced proliferation of lymphoid cells and are obtainable by immunizing with mammalian cells which have been transfected with a c-kit sequence that can be expressed in these cells and immortalizing the spleen cells of the immunized animals, identifying those hybridoma cells which produce the desired antibody by determining the binding of the antibody obtained to the c-kit receptor as well as by determining the effect of this antibody on the proliferation of lymphoid cells, identifying those hybridoma cells whose culture supernatant has a stimulatory effect in this process, cloning these hybridoma cells and isolating the antibodies produced by these clones according to known methods.

The cell lines DSM ACC 2007, DSM ACC 2008 and DSM ACC 2009 are also a subject matter of the invention.

It surprisingly turned out that it is possible to assess the malignancy of tumours in the area of haematopoietic cells, of seminomas as well as of small-celled lung carcinoma using the monoclonal antibodies against c-kit according to the present invention which provides valuable information for therapy.

The invention therefore also concerns a method for detecting the malignancy of tumours of haematopoietic cells, of seminomas and small-celled lung carcinoma in which a tissue sample is incubated with at least one monoclonal antibody against the c-kit receptor and subsequently bound antibodies are determined by means of known methods.

In a preferred embodiment the tissue sample is incubated with an antibody according to the present invention against the c-kit receptor. In this case an antibody of the IgG isotype is preferably used. Fab or F(ab')$_2$ fragments can also be used.

In order to detect bound antibody against the c-kit receptor an incubation is for example carried out with a second antibody against murine Fc $\gamma$ that is labelled before or after binding to the c-kit antibody. An enzyme, or a fluorescent or chemiluminescent dye is usually used as the label.

Malignant tumours of haematopoietic cells, malignant seminomas and, when using monoclonal antibodies which bind to the c-kit receptor in an equivalent manner to the antibodies produced by the cell lines DSM ACC 2007 or DSM ACC 2009, also small-celled lung carcinomas show a positive signal in this method.

A further use of the monoclonal antibodies against the human c-kit receptor according to the present invention which inhibit stimulation of the proliferation of lymphoid cells by SCF, is to use them to produce a therapeutic agent for the treatment of myeloid leukemia.

The cell lines according to the present invention DSM ACC 2006, DSM ACC 2007, DSM ACC 2008 and DSM ACC 2009 were deposited on 23.05.1991 at the "Deutsche Sammlung yon Mikroorganismen und Zellkulturen GmbH, Mascheroder Weg 1b, D-3300 Braunschweig.

The invention is elucidated by the following examples in conjunction with the figure.

FIG. 1 shows the stimulation of SCF-induced proliferation of lymphoid cells by the monoclonal antibody DSM ACC 2009 and the inhibition of the SCF-induced proliferation of lymphoid cells by the monoclonal antibody DSM ACC 2007. In each case the proportion of cells proliferating is shown after incubation of AML cells at 37° C. with medium (●), 100 μg/ml SCF (∇), 2 μg/ml of the monoclonal antibody DSM ACC 2007 (▼) or DSM ACC 2009 (Δ), as well as after preincubation with the monoclonal antibodies DSM ACC 2007 (□) and DSM ACC 2009 (▲) for 30 minutes at 4° C. before stimulation with SCF.

Example 1

Production of monoclonal antibodies against the human c-kit receptor

The human c-kit gene is cloned as described by Yarden et al. (EMBO Journal, volume 6 (1987), 3341–3351) and expressed in NIH-3T3 cells. Balb/c mice are immunized intraperitoneally with 5000,000 of these transfected NIH-3T3 cells that express c-kit. This immunization is repeated at intervals of ca. 4 weeks. The total immunization period is 6 months. Subsequently the animals are in addition twice immunized with c-kit enriched with wheat germ agglutinin (see example 2); the last of these immunizations is carried out intravenously. Three days after this last immunization, the spleen cells of the immunized animals are immortalized with the myeloma cell line P3X63-Ag8.653 (ATCC CRL 1580 ).

The fusion of the spleen cells with the myeloma cell line is carried out according to the standard method according to J. of Imm. Meth., 39 (1980), 285–308. The fusion ratio of spleen cells: myeloma cells is 1:1 in this case. The fusion products are sown out on 24-well culture plates of the Greiner Company with $5 \times 10^4$ peritoneal exudate cells of the mouse. Positive primary cultures (determined according to example 3) are cloned two weeks after fusion with the aid of a fluorescence-activated cell sorter (Becton Dickinson). For this the cells are placed individually in 96-well microtitre plates and fed with HECS medium (Tecnomara). Subsequently commercial RPMI-1640 medium containing 10% foetal calf serum is used as the culture medium.

In order to produce the monoclonal antibodies the hybridoma cell clones obtained in this way are expanded in vivo. For this mice pretreated with Pristan (Sigma) are inoculated intraperitoneally with $5 \times 10^6$ hybridoma cells. After 10–15 days, 2–3 ml ascites is taken from each mouse and the monoclonal antibody is isolated from this according to conventional methods. The yield is about 5 mg IgG/ml ascites.

EXAMPLE 2

Concentration of the c-kit receptor protein by means of wheat germ agglutinin Agarose The transfected NIH-3T3 cell line c-kit that expresses c-kit is cultured until confluent in roller flasks in DMEM/F12 (1:1) medium which contains 10% FCS and 2 mmol/l glutamine. The cells are subsequently lysed in 20 ml lysis buffer. The lysis buffer contains 50 mmol/l Hepes pH 7.5; 150 mmol/l sodium chloride; 1.5 mmol/l MgCl$_2$; 1 mmol/l EGTA; 1% Triton X-100; 10% glycerol and 4 μg/ml PMSF.

The lysate is centrifuged at 100000 g for 1 hour, the supernatant is diluted 1:1 with Her2x buffer and bound overnight at 40° C. in a batch process to wheat germ agglutinin-Agarose (Sigma) (Her2x buffer: 50 mmol/l Hepes pH 7.2; 150 mmol/l sodium chloride; 1% Triton X-100; 10% glycerol and 4 µg/ml PMSF). Subsequently the wheat germ agglutinin-Agarose is washed with 10 volumes Her2x buffer and finally c-kit receptor protein is eluted with 0.3 mol/l N-acetyl-glucosamine in Her2x buffer.

EXAMPLE 3

Determination of the specificity of the antibodies which are produced

An enzyme-linked immunosorbent assay (ELISA) is used to determine the specificity of the antibodies in the culture supernatant of the hybridoma cells.

For this, 96-well microtitre plates (Nunc) are coated with 100 µl c-kit antigen (isolated according to example 2; 5 µg/ml in carbonate buffer, Boehringer Mannheim, Catalogue No. 726559), incubated with 100 µl culture supernatant (diluted 1:25 with PBS (according to Dulbecco and Vogt, J. Exp. Med. 99 (1954), 167–182) for 2 hours at room temperature and washed with 3×350 µl PBS/0.05% Tween 20. Afterwards it is incubated with POD-labelled sheep anti-mouse IgG (10 mU; Boehringer Mannheim, Catalogue No. 1317377) for 15 minutes at room temperature, washed with 3×350 µl PBS/0.05% Tween 20 and the test reaction is started with 100 µl ABTS® (1 mg/ml, Boehringer Mannhein, Catalogue No 756407) in 40 mmol/l citrate buffer pH 4.4 which contains 3.25 mmol/l sodium perborate (Boehringer Mannheim, Catalogue No. 1204 530). After a 20 minute incubation at room temperature, the absorbances are determined in a photometer at 405 nm.

EXAMPLE 4

Determination of the effect of the antibodies which are produced on the SCF-induced proliferation of lymphoid cells and on the binding of growth factors.

Lymphocytes are isolated by density gradient centrifugation ("Lymphozyten-Trennmedium" Boehringer Mannheim GmbH, Catalogue No. 295 949) and adjusted to a cell titre of $1 \times 10^6$ cells/ml in complete RPMI 1640 (10% foetal calf serum, 2 mmmol/l glutamine, 1% vitamin solution (Boehringer Mannheim GmbH, Catalogue No. 210 307), 100 IU/ml penicillin and 100 µg/ml streptomycin). 100 µl of this cell suspension is incubated together with 10 µl recombinant human SCF (Amgen Thousand Oaks U.S.A.; final concentration 100 ng/ml) and with 2 µg/ml of the monoclonal antibody to be examined in parallel experiments for 30 minutes at 37° C. In two further parallel experiments firstly a preincubation with 2 µg/ml of the monoclonal antibody to be examined is carried out for 30 minutes at 4° C. and subsequently 100 ng/ml SCF is added. Subsequently, those cells which have bound a monoclonal antibody to be examined are stained by fluorescence labelling with FITC-coupled anti-mouse immunoglobulin from sheep (Boehringer Mannheim GmbH, Catalogue No. 821 462) and the DNA of these cells is stained by treating the cells with a hypotonic solution of 0.05 mg/ml propidium iodide (Sigma) and 0.1% sodium citrate and the labels are examined in a FACS IV cell sorter (Becton Dickinson). The excitation is carried out at 488 nm, the FITC-labelled cells are measured at 530 nm and the propidium iodide-labelled nuclei are measured at 610 nm. The percentage of proliferating cells is given by the sum of the proportion of cells labelled with propidium iodide which are in the S phase as well as in the G2 and M phase (%S+%G2/M). FIG. 1 shows the stimulating effect of the monoclonal antibody DSM ACC 2009 on the SCF-induced proliferation of lymphoid cells as well as the inhibitory effect of the monoclonal antibody DSM ACC 2007 on the SCF-induced proliferation of lymphoid cells.

The monoclonal antibody DSM ACC 2007 in addition causes an inhibiton of the binding of SCF to the c-kit receptor. In order to detect this effect, the lymphocytes isolated as described above are incubated for 30 minutes on ice in PBS containing 0.01% $NaN_3$ and 2 µg/ml of the monoclonal antibody DSM ACC 2007. Subsequently 125 ng/ml biotinylated SCF is added and the cells are stained with streptavidin-phycoerythrin (Dianova). The evaluation is carried out in a FACS IV cell sorter (Becton Dickinson) at an excitation wavelength of 488 nm and measuring at 570 nm. Compared to a control preparation which was not incubated with the monoclonal antibody DSM ACC 2007, there is a 98% inhibition of the SCF binding to lymphocytes by the monoclonal antibody DSM ACC 2007.

Medium (complete RPMI 1640)

440 ml RPMI 1640 (Boehringer Mannheim BM 209 945) 50 ml foetal calf serum (FCS) (BM 210 471) 5 ml glutamine solution, 200 mmol/l (BM 210 277) 5 ml vitamin solution (1%) (BM 210 307) 1 ml penicillin (50000 IU) and streptomycin (50 mg)

| Vitamin solution (BM 210 307): | | | |
|---|---|---|---|
| | mg/100 ml | | mg/100 ml |
| Ca-D(+)-pantothenate | 10.0 | nicotinamide | 10.0 |
| choline chloride | 10.0 | pyridoxal.HCl | 10.0 |
| folic acid | 10.0 | riboflavin | 1.0 |
| meso-inositol | 20.0 | thiamine.HCl | 10.0 |

EXAMPLE 5

Determination of the epitope overlap of antibodies against c-kit

A competitive enzyme immunoassay is carried out to detect the epitope overlap of an antibody with the monoclonal antibody DSM ACC 2007. For this the c-kit receptor protein concentrated according to example 2 is firstly biotinylated with D-biotinyl-ε-amidocaproic acid-N-hydroxysuccinimide ester (Boehringer Mannheim, Catalogue No. 1008960) according to the manufacturer's instructions. 300 ng of this biotinylated antigen is bound in a volume of 100 µl PBS to a streptavidin-coated microtitre plate (produced according to EP-A 0 344 578) by incubating for 1 hour at room temperature After washing four times with PBS/0.05% Tween 20, it is incubated simultaneously for 90 minutes at room temperature with the monoclonal antibody DSM ACC 2007 which was labelled with peroxidase (final concentration 250 mU/ml) and with the antibody to be assessed. After washing again four times with PBS/0.05% Tween 20, it is incubated for 30 minutes at room temperature with the enzyme-substrate solution ABT® in a buffer containing sodium perborate and subsequently the absorbance at 405 nm is measured as a measure for the amount of bound POD-labelled monoclonal antibody DSM ACC 2007. This value was compared with the absorbance which was obtained when the monoclonal antibody DSM ACC 2007 was incubated alone. When competition of at least 50% is detectable at a $10^5$-fold excess of the antibody to be assessed in relation to the monoclonal antibody DSM ACC 2007 enzyme-conjugate (250 mU/ml) an epitope overlap is present.

EXAMPLE 6

Determination of the expression of the c-kit receptor protein in different tissues and tumours The tissue section to be examined is incubated for 2 hours at 4° C. with a monoclonal antibody against c-kit (DSM ACC 2007, DSM ACC 2009 or DSM ACC 2008, 20 µg/ml in each case). After a washing step (3×5 minutes in PBS/ 0.05% Tween 20) the tissue section is incubated for 1 hour at room temperature with sheep anti-mouse IgG (100 µg/ml, Boehringer Mannheim, Catalogue No. 1092618). Bound antibody is detected by means of a complex of peroxidase and murine anti-peroxidase antibody (250 mU/ml, Boehringer Mannheim, Catalogue No. 1092 626, 1 hour incubation at room temperature). The test reaction is started with diaminobenzidine (1 mg/ml) and evaluated with a microscope.

The following table shows the reactivity determined by this method of the monoclonal antibodies obtained from the cell lines DSM ACC 2007, DSM ACC 2008 and DSM ACC 2009.

| Tissue | monoclonal antibody | | |
| --- | --- | --- | --- |
| | DSM ACC 2007 | DSM ACC 2008 | DSM ACC 2009 |
| seminoma | + | + | + |
| small-celled lung carcinoma | + | − | + |
| healthy lung tissue | − | − | − |

We claim:

1. A hybridoma cell line which produces a monoclonal antibody against the human c-kit receptor wherein the cell line is DSM ACC 2007.

2. A monoclonal antibody against the human c-kit receptor which inhibits the stimulation of the proliferation of lymphoid cells by stem cell factor (SCF) and binds paraffin-treated c-kit receptor, wherein the monoclonal antibody is selected from the group consisting of the monoclonal antibody produced by the cell line DSM ACC 2007 and a monoclonal antibody which binds to the epitope bound by the antibody produced by the cell line DSM ACC 2007, wherein the monoclonal antibody is made by the steps comprising:

a) immunizing an animal with mammalian cells which have been transfected with a c-kit sequence expressed in said mammalian cells, b) immortalizing the spleen cells of the immunized animal to produce hybridomas, c) identifying those hybridomas which produce a monoclonal antibody specific for c-kit by selecting hybridomas producing antibodies that specifically bind to c-kit, d) further identifying, from the hybridomas of step c), hybridomas producing antibodies which inhibit the stimulation of the proliferation of lymphoid cells by stem cell factor (SCF) and bind paraffin treated c-kit receptor, e) cloning the hybridomas identified in step d), and f) isolating the antibody produced by the hybridomas of step e).

3. The monoclonal body of claim 2 which is obtainable from the cell line DSM ACC 2007.

4. A method for testing the malignancy of a tumor selected from the group consisting of tumors of hematopoietic cells, seminomas and small-celled lung carcinoma, comprising a) incubating a tissue sample with at least one monoclonal antibody against the c-kit receptor, wherein the monoclonal antibody is isolated from the cell line DSM ACC 2007, and b) detecting bound antibody.

* * * * *